(12) United States Patent
Fähsing (10) Patent No.: US 11,376,059 B2
(45) Date of Patent: Jul. 5, 2022

(54) ELECTROSURGICAL SYSTEM COMPRISING A MEASURING UNIT

(71) Applicant: OLYMPUS WINTER & IBE GMBH, Hamburg (DE)

(72) Inventor: Thomas Fähsing, Blankenburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 638 days.

(21) Appl. No.: 16/321,434

(22) PCT Filed: Aug. 7, 2017

(86) PCT No.: PCT/EP2017/069968
§ 371 (c)(1),
(2) Date: Jan. 28, 2019

(87) PCT Pub. No.: WO2018/029154
PCT Pub. Date: Feb. 15, 2018

(65) Prior Publication Data
US 2020/0121381 A1 Apr. 23, 2020

(30) Foreign Application Priority Data
Aug. 8, 2016 (DE) ...................... 10 2016 214 704.8

(51) Int. Cl.
*A61B 18/12* (2006.01)
*A61B 18/14* (2006.01)
*A61B 18/00* (2006.01)

(52) U.S. Cl.
CPC .......... *A61B 18/1206* (2013.01); *A61B 18/14* (2013.01); *A61B 2018/00767* (2013.01)

(58) Field of Classification Search
CPC ................ A61B 18/1206; A61B 18/14; A61B 2018/00767; A61B 2018/00702;
(Continued)

(56) References Cited

U.S. PATENT DOCUMENTS

2006/0015095 A1  1/2006 Desinger et al.
2014/0074084 A1* 3/2014 Engeberg ............... A61B 18/14
606/33
(Continued)

FOREIGN PATENT DOCUMENTS

DE  102 24 154 A1  12/2003
DE  10224154 A1 * 12/2003  ......... A61B 18/1477
(Continued)

OTHER PUBLICATIONS

Apr. 7, 2017 Office Action issued in German Patent Application No. 10 2016 214 704.8.
(Continued)

*Primary Examiner* — Khadijeh A Vahdat
(74) *Attorney, Agent, or Firm* — Oliff PLC (57) ABSTRACT

An electrosurgical system for treating tissue, including a first and second electrode; a high-frequency high-voltage supply unit which can be electrically connected to first and second electrode and is designed to supply a specified treatment alternating voltage to electrodes; and a measuring unit which can be electrically connected to first and second electrode and has a measurement voltage supply module that is designed to provide a measurement alternating voltage of at least one first and second frequency, wherein the measuring unit is additionally designed to receive an electric response signal for first and second frequency via first and second electrode and determine at least one property of a tissue located between first and second electrode therefrom. The electrosurgical system relates further to an electrosurgical generator for treating tissue, to a method of operating an electrosurgical system, to using electrosurgical system and to applying the method of operating an electrosurgical system.

9 Claims, 5 Drawing Sheets

(58) Field of Classification Search
CPC ........... A61B 2018/00875; A61B 2018/00636; A61B 2018/00571
USPC .................................................. 606/41–52
See application file for complete search history.

(56) References Cited

U.S. PATENT DOCUMENTS

2014/0364843 A1    12/2014  Paul et al.
2015/0265333 A1*   9/2015   Shin ...................... A61B 5/053
                                                     606/34

FOREIGN PATENT DOCUMENTS

| EP | 2 540 243 A1  | 1/2013 |
| JP | 2005-527306 A | 9/2005 |
| JP | 2009-518151 A | 5/2009 |

OTHER PUBLICATIONS

Oct. 26, 2017 International Search Report issued in International Patent Application No. PCT/EP2017/069968.
Mar. 8, 2021 Office Action issued in Japanese Patent Application No. 2019-506658.
Jul. 2, 2021 Office Action issued in Chinese Patent Application No. 201780046014.9.

\* cited by examiner

ELECTROSURGICAL SYSTEM COMPRISING A MEASURING UNIT

The invention relates to an electrosurgical system for treating tissue. The invention relates further to an electrosurgical generator for treating tissue, to a method of operating an electrosurgical system, to using the electrosurgical system and to applying the method of operating an electrosurgical system.

It is known to treat tissue by means of high-frequency alternating voltage, for example, to cut or coagulate it. During a treatment of body tissue in the context of high-frequency surgery (HF surgery), an impedance of the tissue to be treated can be determined, for example, in order to identify to what extent the tissue has dried out. The object in this regard is to stop the delivery of a treatment alternating voltage suitable for treating the body tissue, as soon as the impedance of the tissue has reached a certain level, in order to avoid, for example, an unwanted carbonation of tissue or a sticking of the tissue to electrodes of a respective HF instrument.

For this purpose, electrosurgical systems are known which are capable of controlling the delivery of treatment alternating voltage depending on the determined impedance of the tissue to be treated.

The invention is based on the object of providing an improved electrosurgical system for treating tissue.

Pursuant to the invention, this object is achieved by means of an electrosurgical system comprising a first electrode and a second electrode, a high-frequency high-voltage supply unit, a measuring unit and a control unit.

The first and second electrode are each designed to be connected to the tissue to be treated in a conductive manner.

The high-frequency high-voltage supply unit can be electrically connected to the first electrode via a first electrical line and to the second electrode via a second electrical line and is designed to supply a predetermined treatment alternating voltage to said electrodes.

The measuring unit can be electrically connected to the first and second electrode and has a measurement voltage supply module that is designed to provide a measurement alternating voltage of at least one first and second frequency, wherein the measuring unit is additionally designed to receive an electric response signal for the first and second frequency via the first and second electrode and determine at least one property of a tissue located between the first and second electrode therefrom.

The control unit is designed to interrupt, during the operation of the electrosurgical system, the electric connection of the high-frequency high-voltage supply unit to the first or the second electrode and ensure the electric connection between the measuring unit and the first and the second electrode at the beginning of the measurement. Furthermore, the control unit is designed to interrupt the electric connection of the measuring unit to the first and the second electrode and ensure the electric connection between the high-frequency high-voltage supply unit and the first and second electrode at the end of the measurement.

The invention includes the recognition that, traditionally, electrical parameters of the tissue to be treated can only be determined at the operating frequency of the high-frequency high-voltage supply unit. As a result, information regarding properties of the tissue is lost when one single operating frequency is used or can at least only be determined insufficiently.

Therefore, it is advantageous to use a separate measuring unit with a measurement alternating voltage of a first and second frequency in addition to a treatment alternating voltage of the high-frequency high-voltage supply unit. As a result, more information about the tissue to be treated can be determined, which is advantageous with regard to a controlled treatment. Information about the tissue to be treated may, for example, be information on a present tissue condition, such as to what extent the tissue has dried out, or information on a present tissue type.

Furthermore, it is advantageous that the electrosurgical system pursuant to the invention can switch from a treatment state, where a treatment alternating voltage is applied to the tissue, into a measuring state, where a measurement alternating voltage is applied to the tissue, and also back into the treatment state, in accordance with the control exercised via the control unit. This clear separation between the two states of the electrosurgical system makes it possible to clearly differentiate between situations in which the properties of the tissue are being determined and situations in which the tissue is being treated. Both processes can be performed precisely without impacting each other.

A use pursuant to the invention of a measuring circuit controlled separately via the measuring unit improves, in particular, the safety of the electrosurgical system, since the control of the measuring unit does not have a direct impact on an operation of the high-frequency high-voltage supply unit. Thus, the treatment of the tissue can be specified solely by means of the properties of the high-frequency high-voltage supply unit without electrical resistances of the measuring unit impacting the treatment.

Furthermore, the electrosurgical system pursuant to the invention can be used with known electrodes, since the measuring unit and the control unit may be parts of an electrosurgical generator comprising the high-frequency high-voltage supply unit. As a result, it is particularly easy to integrate the electrosurgical system pursuant to the invention into existing HF surgical systems.

The use of variable treatment breaks between the beginning of the measurement and the end of the measurement leads to a separation in time between the measuring of the properties of the tissue and the treatment of said tissue. While the operating frequency of the high-frequency high-voltage supply unit is in a range between 350 and 500 kHz and is usually constant over a treatment period, the measurement alternating voltage of the measuring unit can be varied over time and be in a frequency range that is particularly suitable for measuring the properties of the tissue.

The beginning of a measurement is triggered by an external or internal control, and is the beginning of a process for measuring properties of a tissue to be treated which is executed by the measuring unit and the control unit. In this context, the measuring by means of the measuring unit is preferably performed separately to the controlling of the present electrical connections by means of the control unit.

The first and second electrode may be arranged in a shared electrosurgical instrument. Furthermore, the first or second electrode may be an active electrode, while the respectively other second or first electrode is a passive electrode. The specific characteristics of the electrodes are not relevant to the present invention; the electrosurgical system can, in particular, be combined with all common types of electrodes where the first and second electrode are connected to the tissue to be treated in a conductive manner.

In the following, preferred embodiments of the electrosurgical system pursuant to the invention are described.

In a particularly preferred embodiment, the measuring unit is designed to determine the impedance of the tissue located between the first and second electrode for the measurement alternating voltage with the first and second frequency, respectively. The determination of the impedance is particularly advantageous due to the fact that the dielectric properties of the tissue to be treated can be inferred from it. Thus, for example the percentage of water in the tissue can be determined. For the determination of the impedance, it is sufficient to determine, in addition to the frequency, the measurement alternating voltage and a magnitude of the measurement current. This can be realized via known measuring device arrangements.

In a preferred version of the previous embodiment, the measuring unit is furthermore designed to determine a difference between the impedances of the tissue measured at at least two different frequencies as a relative parameter. In this context, in an example of the version, the impedance difference is the difference between the impedance amounts. The respectively measured impedance values may be represented by measurement values that are two-dimensional, i.e. comprise a real part and an imaginary part. In another example, the impedance difference is the difference between the amounts of the real parts of the measured impedances. The more the tissue coagulates, the smaller becomes the difference so that a level of coagulation is the determined property of the tissue.

In another embodiment, the control unit is electrically connected to the measuring unit and, furthermore, designed to trigger an activation of the measurement alternating voltage with the first frequency through the measurement voltage supply module after the beginning of the measurement and to trigger a deactivation of a measurement alternating voltage of the measurement voltage supply module before the end of the measurement. In this embodiment, a measurement of a measurement alternating voltage will only be started once the measuring unit is electrically connected to the tissue and the connection will only be interrupted once the measurement via the measurement alternating voltage has been completed. This reduces the risk of voltage spikes at switches controlled by the control unit and a controlled, at least provisional, completion of the desired measurement process is ensured.

The determination of the property of the tissue located between the two electrodes is preferably performed in a signal processing module of the measuring unit which receives the electric response signals for the first and second frequency. In one version, the signal processing module of the measuring unit is further connected to a storage module of the measuring unit and designed to determine the property of the tissue based on a comparison with a value stored in the storage module.

Preferably, measurement alternating voltages with more than two different frequencies will be used in the context of a measurement process performed by the measuring unit. Preferably, a response signal is determined for a plurality of frequencies of a frequency range. For example, the first frequency may be in the frequency band between 10 kHz and 50 kHZ, the second frequency may be in the frequency band between 200 kHz and 600 kHz, and a third frequency may be in a frequency band between 800 kHz and 1.2 MHz. In one version of this embodiment, a plurality of differences between measured impedances of the tissue is also determined in accordance with the plurality of frequencies.

In another embodiment, the period of time between the beginning of the measurement and the end of the measurement is a predefined measurement duration. In this embodiment, the triggering of the end of the measurement does not require a separate internal or external input, since the time of the end of the measurement is already defined through a triggering of the beginning of the measurement.

In an alternative embodiment, the measurement duration between the beginning of the measurement and the end of the measurement is not predefined. In this embodiment, the measurement process of the measuring unit is continued until the measuring unit receives a signal that triggers the end of the measurement through the measuring unit and the control unit.

In one embodiment, the electrosurgical system is configured such that the beginning of the measurement is triggered automatically by the control unit in certain, in particular predefined, time intervals. In this embodiment, no additional signal, for example through user input, is required to trigger the beginning of the measurement. Advantageously, this can ensure a regular measuring of the property of the tissue without requiring an additional operating unit or any manual user input. This reduces the risk that, during an operation of the electrosurgical system pursuant to the invention, the property of the tissue might not be determined often enough. Furthermore, the automated triggering of the beginning of the measurement facilitates the automation of the entire treatment of the tissue by means of the electrosurgical system.

Preferably, in the case of the electrosurgical system pursuant to the invention, there will be regular switching between a treatment state, in which the treatment alternating voltage is applied to the tissue, and a measuring state, during which the measuring unit supplies the measurement alternating voltage to the tissue.

In another embodiment, the electrosurgical system is designed to manually trigger the beginning of the measurement, wherein a user interface is designed to provide a corresponding trigger signal to the control unit in case of a user input. The user interface may, for example, be a button that the user of the electrosurgical system pushes at regular intervals.

In a particularly preferred embodiment, the control unit is designed to control the electric connection of the high-frequency high-voltage supply unit to the first or second electrode via a first switch and to control the electric connection of the measuring unit to the first or second electrode via a second switch, wherein the measuring unit and the second switch are arranged parallel to the high-frequency high-voltage supply unit and the first switch, in a circuit formed by the electrosurgical system. Such a parallel arrangement of the circuits of the measuring unit and the high-frequency high-voltage supply unit of the electrosurgical system makes it possible to ensure that the device resistances of the measuring unit do not impact the treatment of the tissue by means of the electrosurgical system. Furthermore, the use of the first and second switch allows a complete electronic decoupling of a circuit of the measuring unit in the context of a measuring process from the circuit of the high-frequency high-voltage supply unit during the treatment process.

In a particularly preferred embodiment of the electrosurgical system, the first and second switch are formed by field-effect transistors that are connected anti-serially to each other. In this context, the anti-serial connection makes it possible to control the first and second switch via a single-control signal. As a result, the controlling of the first switch and the controlling of the second switch at the beginning of the measurement and at the end of the measurement can, respectively, be advantageously coupled to each other. Furthermore, the use of field-effect transistors allows the use of a very small switching current for switching the first and second switch, respectively. In addition, an arrangement of the first and second switch pursuant to the present embodiment can be realized in a particularly space and cost saving manner.

In a preferred embodiment, the measuring unit is electrically connected to the control unit and designed to change an operating state of the control unit depending on the specific properties of the tissue. In one version of this embodiment, the measuring unit is designed to define a time interval until the next beginning of a measurement that is shorter than the interval before the previous beginning of a measurement, if a difference between the impedances is below a threshold value at different frequencies. Thus, an intensity of the treatment with the high-frequency high-voltage supply unit can be reduced through more frequent treatment breaks in the context of measuring processes, if the tissue to be treated is dried out to a high degree. In another version, the measuring unit is designed to trigger a switching off of the high-frequency high-voltage supply unit by the control unit if a difference between the impedances is below another threshold value at different frequencies. In the context of this embodiment, an operating state may, for example, be a time interval between subsequent points in time of the beginning of a measurement or a differentiation between an active and an inactive electrosurgical system. The control unit may, in particular, be designed to provide an emergency stop function for the electrosurgical system. An emergency stop is present when the high-frequency high-voltage supply unit is switched off in case of certain parameter ranges for the property of the tissue to be treated.

Pursuant to the invention, in order to achieve the above mentioned object, an electrosurgical generator for treating tissue is proposed as well, wherein said electrosurgical generator comprises a high-frequency high-voltage supply unit, a measuring unit and a control unit. The high-frequency high-voltage supply unit can be electrically connected to a first and second electrode and is designed to supply a specified treatment alternating voltage to said electrodes. The measuring unit can be electrically connected to the first and second electrode and has a measurement voltage supply module that is designed to provide a measurement alternating voltage of at least one first and second frequency, wherein the measuring unit is additionally designed to receive during the operation of the measuring unit an electric response signal for the first and second frequency via the first and second electrode and determine at least one property of a tissue located between the first and second electrode therefrom. Furthermore, the control unit is designed to interrupt during the operation of the electrosurgical generator, the electric connection of the high-frequency high-voltage supply unit to the first or second electrode and ensure the electric connection between the measuring unit and the first or the second electrode at the beginning of a measurement. In addition, the control unit is designed to interrupt the electric connection of the measuring unit to the first or second electrode and ensure the electric connection between the high-frequency high-voltage supply unit and the first and second electrode at the end of the measurement.

In a particularly advantageous embodiment, the electrosurgical generator pursuant to the invention may be provided in a single housing that can be connected to the first and second electrode via corresponding connections or a corresponding connection. Thus, an easy transport of the device and a quick signal transfer between the measuring unit, control unit, and high-frequency high-voltage supply unit can be ensured in an advantageous manner.

Furthermore, a method of operating an electrosurgical system is proposed in order to achieve the above object. The method pursuant to the invention comprises the following method steps:

triggering a beginning of a measurement of the electrosurgical system;

interrupting an electric connection of a high-voltage supply unit to a first or second electrode;

applying a measurement alternating voltage with a first frequency supplied by a measuring unit to the first and second electrode;

receiving an electric response signal for the first frequency and determining a property of a tissue located between the first and second electrode;

applying a measurement alternating voltage with a second frequency supplied by the measuring unit to the first and second electrode;

receiving an electric response signal for the second frequency and determining the property of the tissue located between the first and second electrode;

interrupting an electric connection of the measuring unit to the first or second electrode;

applying a treatment alternating voltage supplied by the high-frequency high-voltage supply unit to the first and second electrode.

The advantage of the method pursuant to the invention is that it can be repeated as often as desired, in order to receive a response signal for the first and second frequency correspondingly often. Accordingly, the property of the tissue located between the first and second electrode can be inferred from the response signal. For example, an impedance of the tissue can be determined. In another version, the difference between the impedances in case of two different frequencies can be used in order to measure the extent to which the tissue has dried out.

Another advantage of the method pursuant to the invention is that it starts with a beginning of a measurement so that it can be ensured that the tissue to be treated has the expected electrical parameters of untreated tissue. This increases the safety of the electrosurgical system that is operated accordingly.

Preferably, the step of applying an additional frequency by means of the measuring unit and of receiving an electronic response signal for the additional frequency and of determining the property of the tissue is performed for more than two frequencies, in particular for frequencies that can be selected from a continuous frequency spectrum.

In another preferred embodiment, the interruption of the electric connection to the measuring unit is preceded by a triggering of the end of the measurement. In this embodiment, a duration of the method pursuant to the invention is not predetermined, but is triggered by an external device, in particular via a user input. Thus, the duration of a measurement by means of the measuring unit can be manually adjusted to a present treatment situation. In an alternative embodiment, an end of the measurement is not triggered, but the treatment alternating voltage is once again applied after a predefined measurement duration.

In a particularly preferred embodiment, the triggering of the beginning of the measurement of the electrosurgical system is performed automatically in certain, in particular predefined, time intervals. These predefined time intervals may be constant, alternating, increasing or decreasing. They may, in particular, depend on a skin type of the tissue to be treated determined before or during the treatment. Such an automated beginning of the measurement reduces in an advantageous manner the number of actions that a user of the respective electrosurgical system must perform.

In one embodiment of the method, the application of a corresponding alternating voltage and the interruption of an electric connection is respectively achieved through a corresponding switching of a first switch for the electric connection of the high-frequency high-voltage supply unit to the first or second electrode and of a second switch for the electric connection of the measuring unit to the first or second electrode. In a particularly preferred version of this embodiment, the first and second switch are formed by field-effect transistors that are connected anti-serially to each other.

Another aspect of the invention relates to the use of the electrosurgical system pursuant to the invention in accordance with at least one of the above described embodiments for treating tissue, in particular for the coagulation or sealing of body tissue.

Another aspect of the invention relates to the application of the method in accordance with at least one of the above described embodiments during the treatment of tissue, in particular during the coagulation or sealing of body tissue.

Figure 1:
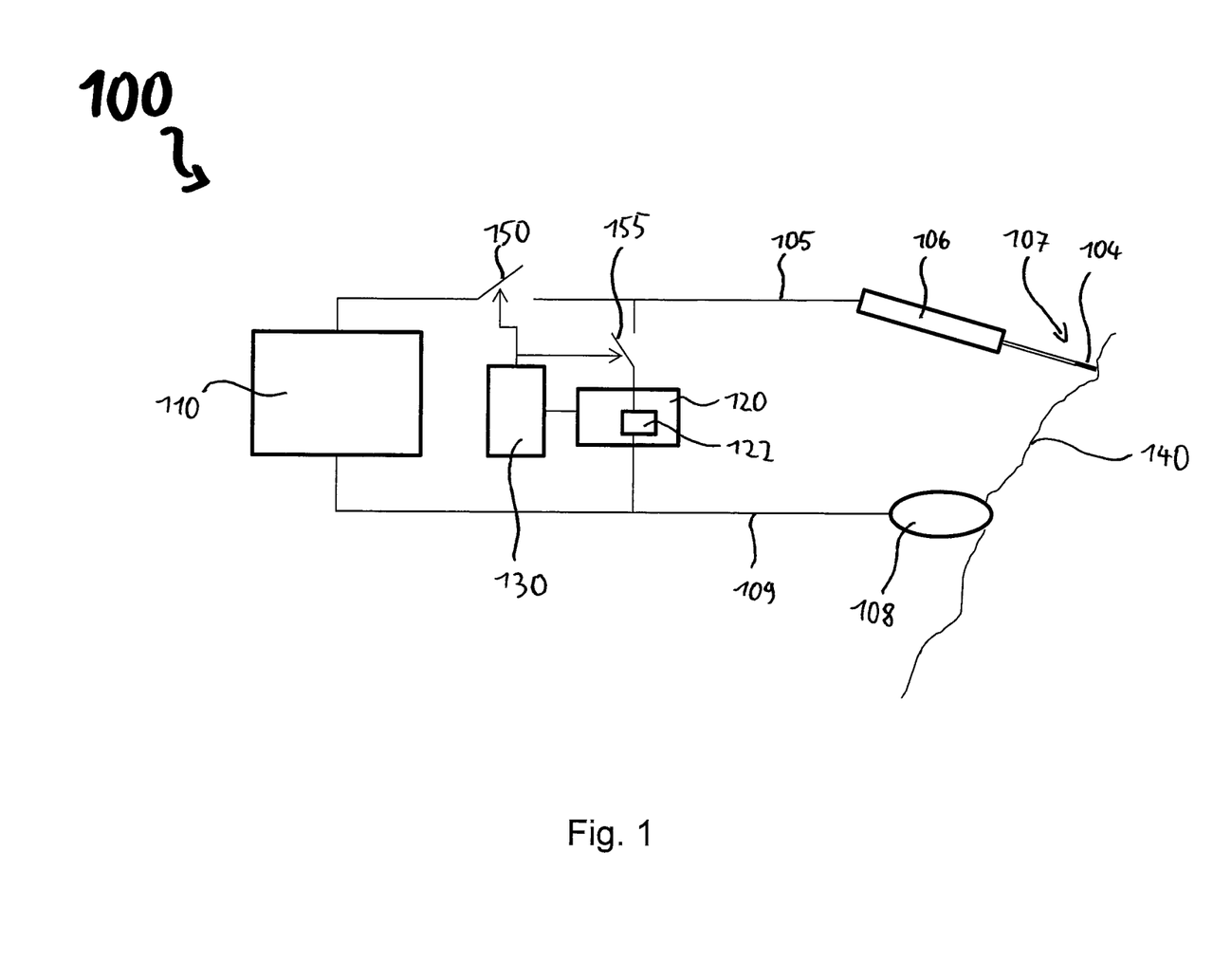
FIG. 1 a first exemplary embodiment of an electrosurgical system pursuant to the invention.

In the following, the invention shall be explained in more detail based on exemplary embodiments with reference to the figures. The figures show the following:

FIG. 1 shows a first exemplary embodiment of an electrosurgical system 100 pursuant to the invention.

The electrosurgical system 100 comprises a first electrode 104 and a second electrode 108, a high-frequency high-voltage supply unit 110, a measuring unit 120 and a control unit 130.

The two electrodes 104, 108 are connected to the tissue 140 to be treated in a conductive manner. In the illustrated exemplary embodiment, the first electrode 104 is an active electrode with a grip area 106 and a distal end 107, and the second electrode 108 is the corresponding passive electrode. A distance between the two electrodes during a treatment on the tissue 140 is chosen such that an electric arc can occur between the two electrodes 104, 108 when an alternating voltage is being applied. In the exemplary embodiment illustrated in FIG. 2, the first and second electrode are present in a shared electrosurgical instrument.

The high-frequency high-voltage supply unit 110 can be electrically connected to the first electrode 104 via a first electrical line 105 and to the second electrode 108 via a second electrical line 109. Furthermore, the high-frequency high-voltage supply unit 110 is designed to supply a predetermined treatment alternating voltage to the two electrodes 104, 108. In the illustrated exemplary embodiment, the alternating voltage is between 350 kHz and 500 kHz.

The measuring unit 120 can also be electrically connected to the first and second electrode 104, 108. Furthermore, the measuring unit 120 comprises a measurement voltage supply module 122 that is designed to provide a measurement alternating voltage of at least one first and second frequency. Furthermore, the measuring unit 120 is designed to receive an electric response signal for the first and second frequency via the first and second electrode 104, 108 and determine at least one property of a tissue 140 located between the first and second electrode 104, 108 therefrom.

The control unit 130 is designed to interrupt during the operation of the electrosurgical system 100 the electric connection of the high-frequency high-voltage supply unit 110 to the first or second electrode 104, 108 and ensure the electric connection between the measuring unit 120 and the first and second electrode 104, 108 at the beginning of a measurement. In addition, the control unit 130 is designed to interrupt the electric connection of the measuring unit 120 to the first or second electrode 104, 108 and ensure the electric connection between the high-frequency high-voltage supply unit 110 and the first and second electrode 104, 108 at the end of the measurement.

Furthermore, FIG. 1 illustrates a first switch 150, by means of which the high-frequency high-voltage supply unit 110 can be disconnected from the first electrode 104. The measuring unit 120 and a second switch 155 are connected in parallel to the high-frequency high-voltage supply unit 110 and the first switch 150. By means of the second switch 155, the measuring unit 120 can be electrically connected to the first electrode 104 or a present electric connection between the measuring unit 120 and the first electrode 104 can be interrupted. In the present case, the first and second switch 150, 155 are designed as field-effect transistors that are connected anti-serially to each other (for reasons of clarity, this is not shown).

In addition, in the illustrated exemplary embodiment, the control unit 130 is designed to perform the beginning of the measurement automatically in predefined time intervals, wherein a measurement performed by the measuring unit 120 between the beginning of the measurement and the end of the measurement has a predefined measurement duration. Therefore, in the present electrosurgical system 100, the treatment process with the treatment alternating voltage and the measuring process with the measurement alternating voltage applied to the electrodes 104, 108 alternate in predefined time intervals. In the present exemplary embodiment, the predefined time intervals are constant. In other exemplary embodiments that are not shown, the predefined time intervals decrease in a predefined manner exponentially over time.

The present electrosurgical system 100 makes it possible to regularly and automatically control properties of the tissue 140 to be treated. Furthermore, a separation in terms of space and time between the treatment process and the measuring process ensures that the two processes do not impact each other.

For reasons of clarity, FIG. 1 does not show that the measuring unit 120 comprises a signal processing module that receives the electric response signals for the first and second frequency. In this context, the signal processing module is designed to determine the property of the tissue 140 on the basis of a comparison with a predetermined value provided to the signal processing module. Furthermore, the present measuring unit 120 is designed to output an information signal on the basis of the determined property of the tissue 140 via a user interface by means of an optical output, for example via a display of the electrosurgical system 100.

In an exemplary embodiment that is not shown, the control unit is connected to a user interface and, furthermore, designed to trigger the beginning of a measurement in case of a manual user input, for example if the user pushes a button.

Figure 2:
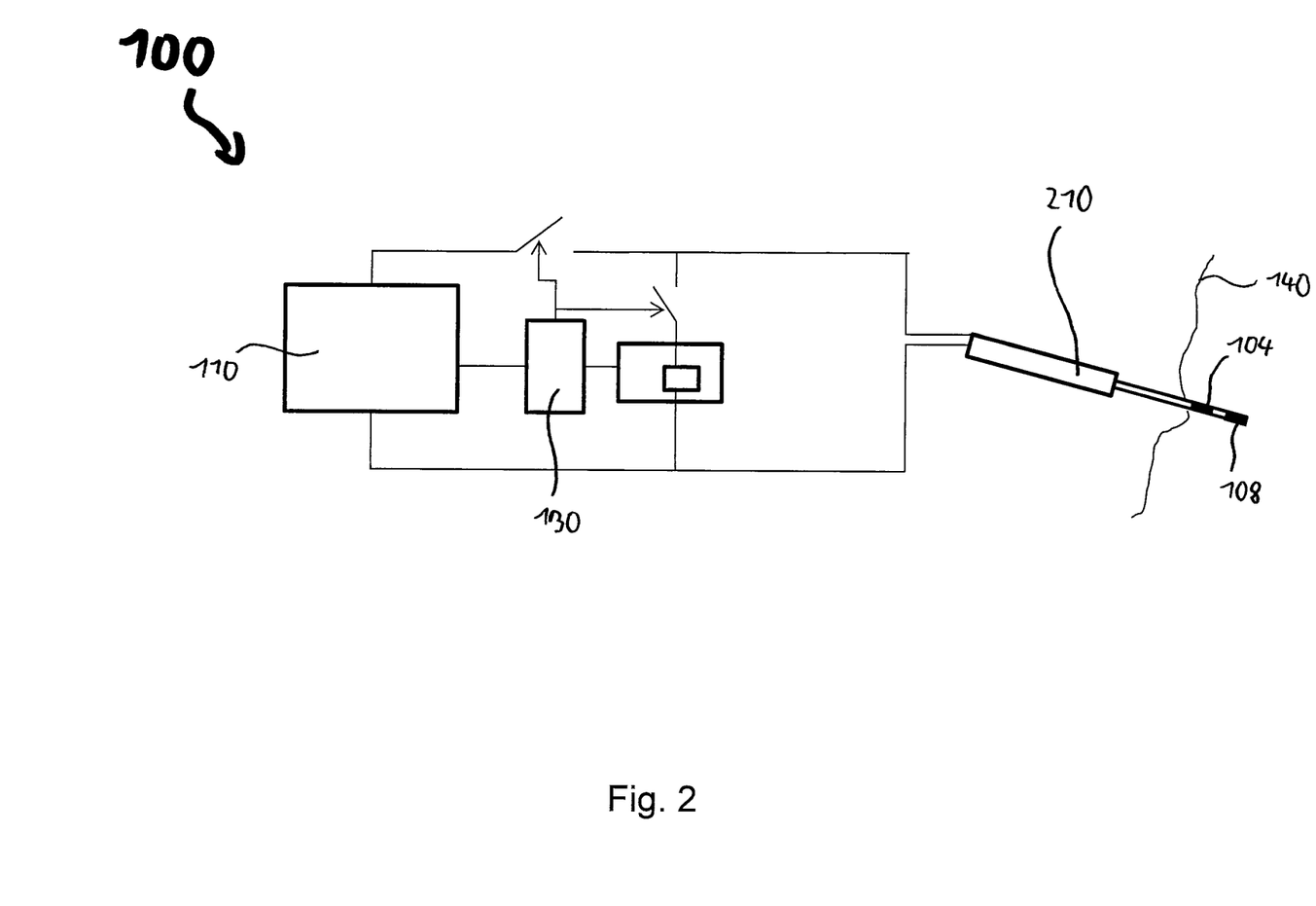
FIG. 2 a second exemplary embodiment of an electrosurgical system pursuant to the invention.

FIG. 2 shows a second exemplary embodiment of an electrosurgical system 100 pursuant to the invention.

The electrosurgical system 100 pursuant to the illustrated second exemplary embodiment differs from the exemplary embodiment shown in FIG. 1 in that the first electrode 104 and the second electrode 108 are arranged at a distal end of a shared electrosurgical instrument 210. In this case, there is a fixed spatial distance between the first electrode 104 and the second electrode 108. A precise position of electrical connection cables within the electrosurgical instrument 210 is not shown in FIG. 2 for reasons of clarity, but well-known in the area of HF surgery.

Furthermore, the electrosurgical instrument 100 shown in FIG. 2 differs from the one in FIG. 1 in that the control unit 130 is electrically connected to the high-frequency high-voltage supply unit 110. In this case, the control unit 130 is, in addition, designed to change an operating state of the high-frequency high-voltage supply unit 110 depending on the property of the tissue 140 to be treated determined by the measuring unit. The high-frequency high-voltage supply unit 110 is, in particular, switched off by the control unit 130, if the impedance measured at the tissue 140 is below a predefined threshold value, i.e. if the tissue 140 has, for example, reached a critical degree of carbonization.

Figure 3:
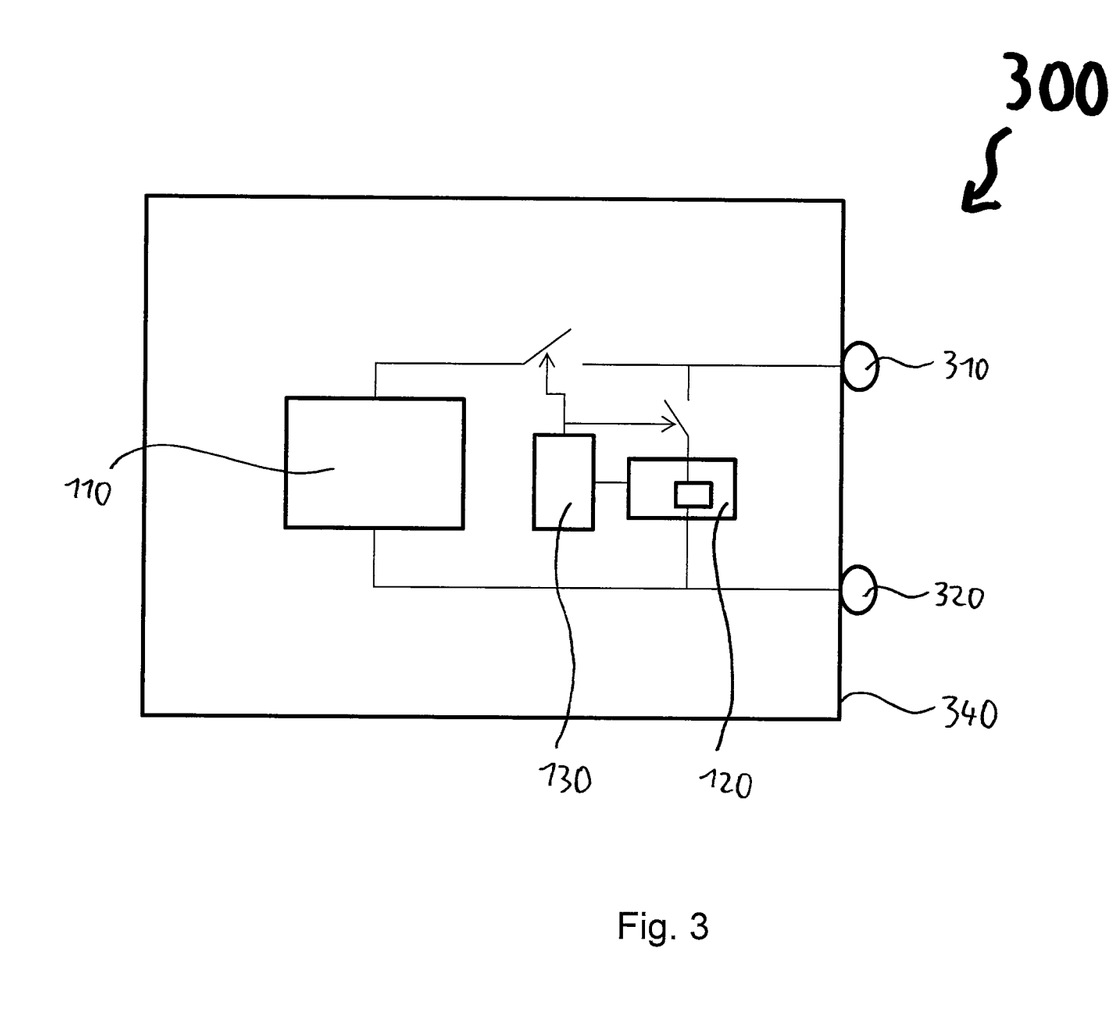
FIG. 3 an exemplary embodiment of an electrosurgical generator pursuant to the invention.

FIG. 3 shows an exemplary embodiment of an electrosurgical generator 300 pursuant to the invention.

The illustrated electrosurgical generator 300 has the design shown in FIG. 1 and the corresponding arrangement of the high-frequency high-voltage unit 110, the measuring unit 120 and the control unit 130. Electrodes can be connected to the illustrated electrosurgical generator 300 via a first connection 310 and a second connection 320. Furthermore, the electrosurgical generator 300 comprises a shared housing 340, in which the first connection 310 and the second connection 320 are arranged, and which includes the high-frequency high-voltage supply unit 110, the measuring unit 120 and the control unit 130.

In this context, the electrosurgical generator 300 is advantageously designed such that commercially available electrodes for the treatment of tissue can be connected to the first connection 310 and the second connection 320.

Figure 4:
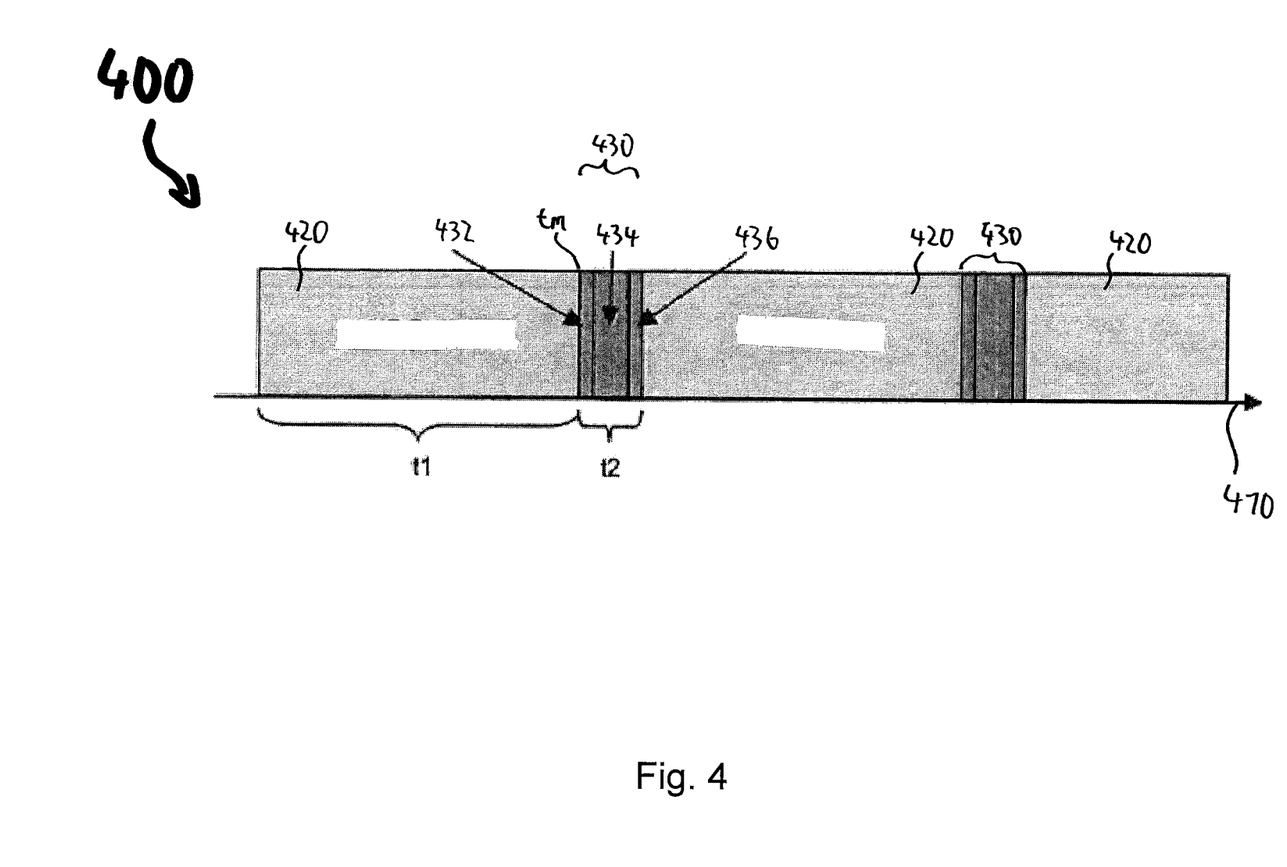
FIG. 4 an illustration of a chronological sequence of the treatment state and the measuring state of the electrosurgical system pursuant to the invention.

FIG. 4 shows an illustration of a chronological sequence 400 of the treatment process 420 and the measuring process 430 of the electrosurgical system pursuant to the invention.

The chronological sequence 400 is shown along a time axis 410. In the illustrated exemplary embodiment, a treatment duration t1 of a treatment process 420 is constant, i.e. it does not change over time. The treatment process 420 is repeated regularly, wherein a measuring process 430 with a measurement duration t2 that is kept constant is always performed between two phases of the treatment process 420. A treatment of the tissue consists of a plurality of treatment processes 420.

The switch between treatment process 420 and measuring process 430 is defined by the point in time tm, at which the measuring process 430 is triggered. In the present exemplary embodiment, the measuring process consists of 3 phases that are comprised of the beginning of the measurement 432, the measurement 434 and the end of the measurement 436. During the beginning of the measurement 432, the electric connection of the electrodes to the high-frequency high-voltage supply unit is interrupted and the electrical connection between the measuring unit and the two electrodes is ensured. The measurement 434 begins with an activation of the measurement alternating voltage for a first frequency. The measurement 434 ends with a switch-off of the measurement alternating voltage. During the end of the measurement 436, the electric connection of the measuring unit to the two electrodes is interrupted and the electric connection between the electrodes and the high-frequency high-voltage supply unit is ensured.

The triggering of the measuring process 430 at the respective point in time tm takes place automatically at regular time intervals of the duration (t1+t2).

In exemplary embodiments that are not illustrated, the beginning of the measurement, the measurement and the end of the measurement are not clearly separated from each other, since a measurement alternating voltage supplied by the measuring unit is present during the complete period of time of treatment so that, after the provision of a corresponding electric connection, a measurement process at the tissue is started. In other exemplary embodiments that are not illustrated, the treatment duration and the measurement duration are not constant over a complete period of time of treatment of the tissue. In one version of the electrosurgical system, in particular, the treatment duration between two measuring processes decreases over the period of time of treatment, for example exponentially.

In one exemplary embodiment that is not illustrated, the treatment duration t1 is 100 ms. In another exemplary embodiment that is not illustrated, the measurement duration t2 is less than 100 ms.

Figure 5:
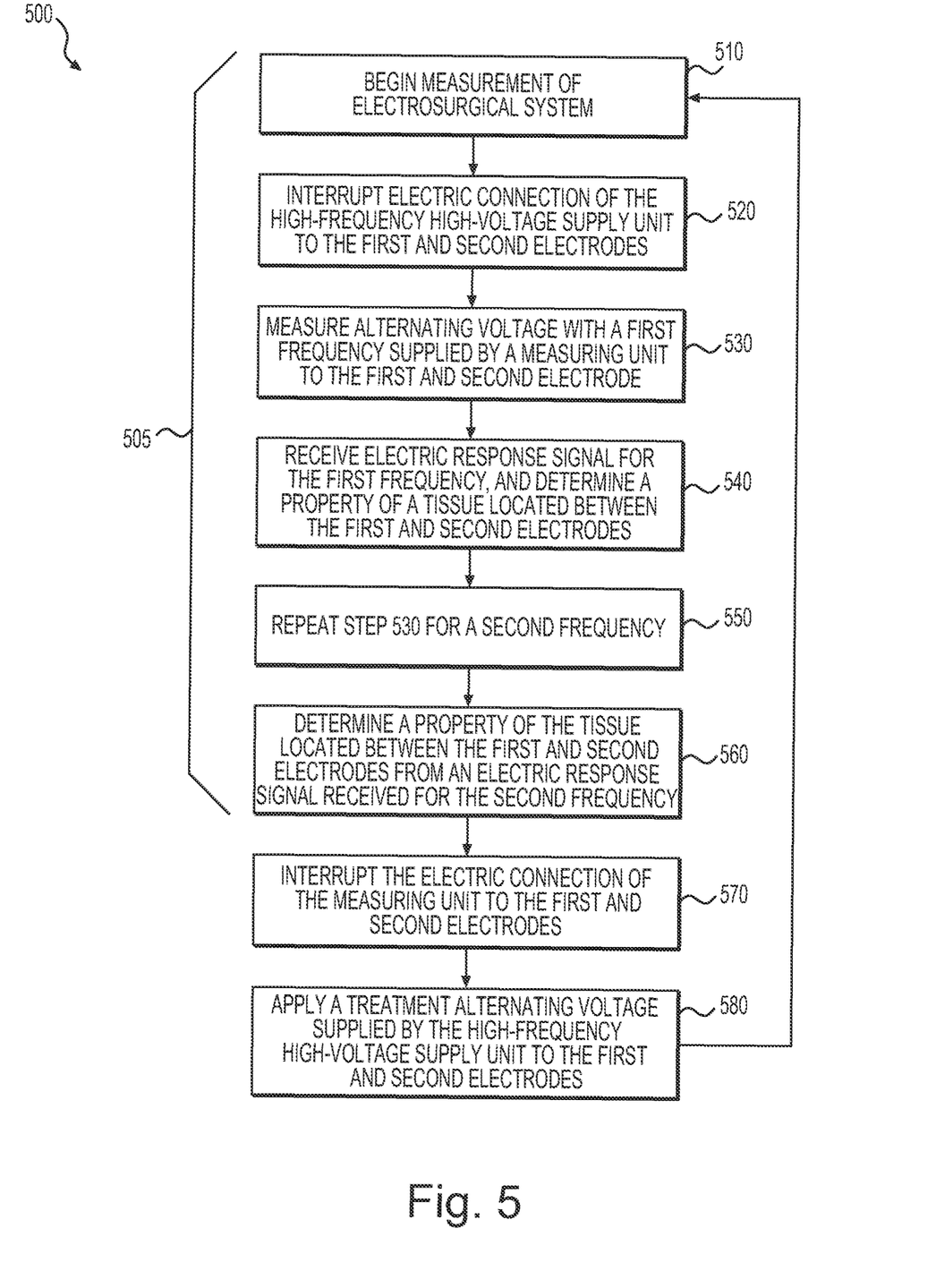
FIG. 5 an exemplary embodiment of a method of operating an electrosurgical system pursuant to the invention.

FIG. 5 shows a method 500 of operating an electrosurgical system comprising the method steps explained in the following.

In a first step 510, a beginning of a measurement of the electrosurgical system is triggered.

Subsequently, an electric connection of the high-frequency high-voltage supply unit to the first and second electrodes is interrupted in another step 520.

Then a measurement alternating voltage with a first frequency supplied by a measuring unit is applied to the first and second electrode in another step 530.

In a next step 540, an electric response signal for the first frequency is received and a property of a tissue located between the first and second electrode is determined.

This is followed by the next step 550, in which step 530 is repeated for a second frequency.

Once again, an electric response signal is received in this context. In said step 560, the property of the tissue located between the first and second electrode is, in turn, inferred from the electric response signal for the second frequency.

At the end of a measuring process 505 performed by means of the steps 510, 520, 530, 540, 550, 560, an electric connection of the measuring unit to the first and second electrode is interrupted in step 570.

Finally, step 580 comprises the application of a treatment alternating voltage supplied by the high-frequency high-voltage supply unit to the first and second electrode.

In the present exemplary embodiment, the first step 510 is repeated at regular intervals. Thus, the illustrated steps 510, 520, 530, 540, 550, 560, 570, 580 are repeated in the illustrated order until an end of the treatment of the tissue.

In exemplary embodiments that are not illustrated, the additional steps of applying a measurement alternating voltage of at least one additional frequency and, respectively, of receiving the electric response signal and, correspondingly, determining a property of the tissue to be treated follow after step 560 and before step 570.

In the present case, the property is the impedance of the tissue, respectively at different frequencies of the applied measurement alternating voltage. In exemplary embodiments that are not illustrated, the step of determining the property includes, in addition, the step of determining an impedance difference between the impedances at different frequencies of the measurement alternating voltage.

LIST OF REFERENCE NUMBERS 100 electrosurgical system
104 first electrode
105 first electrical line
106 grip area
107 distal end
108 second electrode
109 second electrical line
110 high-frequency high-voltage power supply unit
120 measuring unit
122 measurement voltage supply module
130 control unit
140 tissue
150 first switch
155 second switch
210 electrosurgical instrument
300 electrosurgical generator
310 first connection
320 second connection
340 housing
400 chronological sequence
410 time axis
420 treatment process
430, 505 measuring process
432 beginning of the measurement
434 measurement
436 end of the measurement
500 method
510 first method step
520, 530, 540, process steps of the measuring process within the method 550, 560,570
580 end of the measuring process within the method
t1 treatment duration
t2 measurement duration
tm switch from treatment process to measuring process

The invention claimed is:

1. An electrosurgical system for treating tissue, the electrosurgical system comprising:
   a first electrode and a second electrode that are each configured to be connected to the tissue to be treated in a conductive manner; and
   an electrosurgical generator including:
      a high-frequency high-voltage supply device that is electrically connected to the first electrode via a first electrical line and electrically connected to the second electrode via a second electrical line, the high-frequency high-voltage supply device being configured to supply a predetermined treatment alternating voltage to the first electrode and the second electrode;
      a measuring unit that is separate and independent from the high-frequency high-voltage supply device, the measuring unit being electrically connected to the first electrode and the second electrode, the measuring unit including a measurement voltage supply module that supplies a measurement alternating voltage of a first frequency and a second frequency and supplies a treatment alternating voltage of the high-frequency high-voltage supply device, the measuring unit being configured to receive an electric response signal for the first frequency and the second frequency via the first electrode and the second electrode, and the measuring unit being configured to determine at least one property of the tissue located between the first electrode and the second electrode based on the received electric response signal; and
   a control unit that, during operation of the electrosurgical system, is configured to (i) interrupt the electric connection of the high-frequency high-voltage supply device to the first electrode or the second electrode, and maintain the electric connection between the measuring unit and the first electrode and the second electrode at a beginning of a measurement by the measuring unit, and (ii) interrupt the electric connection of the measuring unit to the first electrode or the second electrode, and maintain the electric connection between the high-frequency high-voltage supply device and the first electrode and the second electrode at an end of the measurement by the measuring unit.

2. The electrosurgical system pursuant to claim 1, wherein the measuring unit is configured to determine an impedance of the tissue located between the first electrode and the second electrode based on the measurement alternating voltage with the first frequency and the second frequency, respectively.

3. The electrosurgical system pursuant to claim 1, wherein the control unit is electrically connected to the measuring unit, and the control unit is configured to trigger an activation of the measurement alternating voltage with the first frequency through the measurement voltage supply module after the beginning of the measurement and to trigger a deactivation of the measurement alternating voltage of the measurement voltage supply module at the end of the measurement.

4. The electrosurgical system pursuant to claim 1, wherein a period of time between the beginning of the measurement and the end of the measurement is a predefined measurement duration.

5. The electrosurgical system pursuant to claim 4, wherein the beginning of the measurement is triggered automatically at certain time intervals by the control unit.

6. The electrosurgical system pursuant to claim 1, wherein:
   the control unit is configured to control the electric connection of the high-frequency high-voltage supply device to the first electrode or the second electrode via a first switch and to control the electric connection of the measuring unit to the first electrode or the second electrode via a second switch, and
   the measuring unit and the second switch are arranged parallel to the high-frequency high-voltage supply device and the first switch, in an electric circuit formed by the electrosurgical system.

7. The electrosurgical system pursuant to claim 6, wherein the first switch and the second switch are formed by field-effect transistors that are connected anti-serially to each other.

8. The electrosurgical system pursuant to claim 1, wherein the measuring unit is electrically connected to the control unit, and the measuring unit is configured to change an operating state of the control unit depending on the determined properties of the tissue.

9. An electrosurgical generator for treating tissue, the electrosurgical generator comprising:
   a high-frequency high-voltage supply device that is electrically connected to a first electrode and a second electrode, the high-frequency high-voltage supply device being configured to supply a specified treatment alternating voltage to the first electrode and the second electrode;

a measuring unit that is separate and independent from the high-frequency high-voltage supply device, the measuring unit being electrically connected to the first electrode and the second electrode, the measuring unit including a measurement voltage supply module that supplies a measurement alternating voltage of a first frequency and a second frequency and supplies a treatment alternating voltage of the high-frequency high-voltage supply device, the measuring unit being configured to receive, during operation of the measuring unit, an electric response signal for the first frequency and the second frequency via the first electrode and the second electrode, and the measuring unit being configured to determine at least one property of the tissue located between the first electrode and the second electrode based on the received electric response signal; and a control unit that, during the operation of the electrosurgical generator, is configured to (i) interrupt the electric connection of the high-frequency high-voltage supply device to the first electrode or the second electrode, and maintain an electric connection between the measuring unit and the first electrode and the second electrode at a beginning of a measurement by the measuring unit, and (ii) interrupt the electric connection of the measuring unit to the first electrode or the second electrode, and maintain the electric connection between the high-frequency high-voltage supply device and the first electrode or the second electrode at an end of the measurement by the measuring unit.

* * * * *